(12) United States Patent
Wilson et al.

(10) Patent No.: US 11,173,068 B2
(45) Date of Patent: *Nov. 16, 2021

(54) TEAR-OFF LENS CAPTURE

(71) Applicant: Racing Optics, Inc., Las Vegas, NV (US)

(72) Inventors: Bart E. Wilson, Las Vegas, NV (US); Stephen S. Wilson, Las Vegas, NV (US); Maxwell C. Klein, Las Vegas, NV (US)

(73) Assignee: Racing Optics, Inc., Las Vegas, NV (US)

( * ) Notice: Subject to any disclaimer, the term of this patent is extended or adjusted under 35 U.S.C. 154(b) by 387 days.

This patent is subject to a terminal disclaimer.

(21) Appl. No.: 15/918,172

(22) Filed: Mar. 12, 2018

(65) Prior Publication Data

US 2018/0200114 A1    Jul. 19, 2018

Related U.S. Application Data

(63) Continuation of application No. 15/175,623, filed on Jun. 7, 2016, now Pat. No. 9,918,876.

(Continued)

(51) Int. Cl.
 *A61F 9/02* (2006.01)
 *A42B 3/26* (2006.01)

(52) U.S. Cl.
 CPC .............. *A61F 9/025* (2013.01); *A61F 9/029* (2013.01); *A42B 3/26* (2013.01); *A61F 9/027* (2013.01)

(58) Field of Classification Search
 CPC .......... A61F 9/025; A61F 9/029; A61F 9/027; A42B 3/26

(Continued)

(56) References Cited

U.S. PATENT DOCUMENTS 3,952,331 A 4/1976 Melville
4,076,373 A 2/1978 Moretti
(Continued)

FOREIGN PATENT DOCUMENTS

WO 2014093514 A1 6/2014
WO 2017048797 A1 3/2017

OTHER PUBLICATIONS

International Search Report and Written Opinion for Application No. PCT/US2016/051662, dated Nov. 15, 2016, 13 pages.

*Primary Examiner* — Nathan E Durham
*Assistant Examiner* — Abby M Spatz
(74) *Attorney, Agent, or Firm* — Fitch, Even, Tabin & Flannery, LLP

(57) ABSTRACT

A tear-off capture system includes an eye protector with a base lens. The eye protector has a retention mechanism mounted on one side, and a support mechanism that supports the eye protector on the head of a wearer. A two-tabbed stack of laminated tear-off lenses mounts to the eye protector via an adhesive. The stack mounts so that the first tab of the stack aligns with the first side of the eye protector and the second tab engages with the retention mechanism. Via the second tab and the retention mechanism, released tear-off layers are directed toward the second side of the eye protector away from the base lens. A capturer helps hold the initially released tear-off layer to the eye protector. An exposed tacky surface on each released tear-off helps hold the subsequently removed tear-off layers.

16 Claims, 9 Drawing Sheets

Related U.S. Application Data

(60) Provisional application No. 62/219,390, filed on Sep. 16, 2015.

(58) Field of Classification Search
USPC .......................................................... 2/426
See application file for complete search history.

(56) References Cited

U.S. PATENT DOCUMENTS

| | | |
|---|---|---|
| 4,138,746 A | 2/1979 | Bergmann |
| D280,994 S | 10/1985 | Abate |
| 4,716,601 A * | 1/1988 | McNeal .................. A61F 9/025 2/434 |
| D319,449 S | 8/1991 | Millar |
| 5,420,649 A | 5/1995 | Lewis |
| 5,592,698 A | 1/1997 | Woods |
| 5,671,483 A | 9/1997 | Reuber |
| 5,685,022 A | 11/1997 | Essman |
| 5,740,560 A | 4/1998 | Muoio |
| 5,809,580 A | 9/1998 | Arnette |
| 5,940,892 A | 8/1999 | Morgan |
| 6,085,358 A | 7/2000 | Cogan |
| 6,308,711 B1 | 10/2001 | Goldberg |
| 6,388,813 B1 | 5/2002 | Wilson |
| 6,536,045 B1 | 3/2003 | Wilson |
| 6,847,492 B2 | 1/2005 | Wilson |
| 6,870,686 B2 | 3/2005 | Wilson |
| 7,184,217 B2 | 2/2007 | Wilson |
| 7,200,875 B2 | 4/2007 | Dondero |
| D596,220 S | 7/2009 | Decent |
| 8,261,375 B1 | 9/2012 | Reaux |
| 8,693,102 B2 | 4/2014 | Wilson |
| 8,974,620 B2 | 3/2015 | Wilson |
| 9,104,256 B2 | 8/2015 | Wilson |
| 9,128,545 B2 | 9/2015 | Wilson |
| 9,274,625 B2 | 3/2016 | Wilson |
| 9,295,297 B2 | 3/2016 | Wilson |
| D768,748 S | 10/2016 | Yoo |
| D792,498 S | 7/2017 | Ohta |
| D792,920 S | 7/2017 | Ohta |
| 2002/0109922 A1 * | 8/2002 | Wilson .................. A42B 3/26 359/630 |
| 2005/0060781 A1 | 3/2005 | Landers |
| 2009/0119823 A1 | 5/2009 | Lee |
| 2011/0219508 A1 * | 9/2011 | Hill .................. A42B 1/247 2/10 |
| 2012/0137398 A1 | 6/2012 | Arnold |
| 2014/0220283 A1 | 8/2014 | Wilson |
| 2014/0247489 A1 | 9/2014 | Wilson |
| 2014/0352041 A1 | 12/2014 | O'Neal |
| 2015/0013891 A1 | 1/2015 | Wilson |
| 2015/0177863 A1 | 6/2015 | Wilson |
| 2015/0309609 A1 | 10/2015 | Wilson |
| 2016/0062138 A1 | 3/2016 | Coty |
| 2016/0062149 A1 | 3/2016 | Gerton |
| 2016/0166435 A1 | 6/2016 | Wilson |
| 2016/0242963 A1 | 8/2016 | Wilson |

\* cited by examiner

TEAR-OFF LENS CAPTURE

RELATED APPLICATIONS

This application is a continuation of prior application Ser. No. 15/175,623, filed on Jun. 7, 2016, which claims priority to U.S. provisional application No. 62/219,390, filed on Sep. 16, 2015, which are hereby incorporated by reference in their entirety.

TECHNICAL FIELD

The present disclosure generally relates to tear-off lenses. More specifically, the present disclosure relates to the capture of laminated lenses torn away from an eye protector.

BACKGROUND

Laminated stacks of tear away lenses (i.e., tear-offs) are used in connection with eye protectors to help provide a clear field of view. Tear-offs are used in a variety of different fields and environments where dirt, fluids, or debris tend to spatter onto lenses and occlude the field of vision of the eye protectors. For example, tear-offs can be used in connection with racing (e.g., auto racing, motorcycle racing, bike racing), outdoor sports (e.g., skiing, mountain biking, paintball), medicine (e.g., surgery, dental procedures), painting, welding, construction, and countless other activities and practices.

Tear-off stacks can be applied to, or used in connection with, a base lens of an eye protector, such as glasses, visors, goggles, face shields, and the like. If and when the protector and/or the stack becomes soiled, for instance, from water, mud, dirt, debris, blood, or other spatter, the wearer can simply remove the upper-most tear-off layer by peeling or tearing it away to expose a clean surface. The removed, or torn-off layer, can then be discarded or disposed.

In many environments, the wearer tearing away a tear-off layer will not have the ability to properly dispose of a removed layer. For instance, racers and surgeons may not have the time, nor the ability to take their concentration away from the task at hand to dispose of a torn-away layer in an environmentally friendly manner. As a result, tear-offs can often end up as litter or improperly disposed trash, which can be unsightly and not environmentally friendly.

SUMMARY

The present disclosure presents embodiments of a system and/or kit (or components thereof) for capturing tear-off lenses released from a lens stack. The present disclosure also presents examples of methods for using and/or manufacturing such systems, kits, and/or related components.

In one example, a system includes an eye protector with a retention mechanism, and a stack of tear-off lenses mountable to (or mounted on) the eye protector. The exemplary eye protector (which can be goggles, a visor, a face shield, glasses, or the like) includes a base lens layer that protects the eyes. The exemplary lens stack comprises a plurality of tear-off lenses laminated together. The lens stack mounts to the base lens of the eye protector via an adhesive layer on a lower (or inward) surface of the stack. The laminated lens stack has a central viewing area that generally corresponds to the shape of the base lens layer of the eye protector, and two tabs that extend from opposing sides of the central viewing area. One of those tabs is configured to interact with a retention mechanism on the eye protector. The retention mechanism and corresponding tab interact so that a mounted lens stack is placed in tension when installed on the eye protector. The tension creates a bias or tendency for the lens stack to pull toward a side of the eye protector, away from the base lens.

In operation, the lens stack and the retention mechanism can interact by inserting the tab of the stack through a slot in the retention mechanism so that the tab extends partially over the base lens of the eye protector, and so that the central portion of the lens stack extends away from the side of the lens protector. The tab can then be hooked or otherwise connected to the retention mechanism, for example, by winding the inserted tab upwards and hooking a hole on the tab onto a pin, peg, or other similar holding structure on the retention mechanism. The lens stack can then be mounted to the eye protector by wrapping the stack around the retention mechanism, thereby creating a wound loop, and adhering the stack to the base lens layer. The wound loop creates tension that biases the released tear-off layers of the stack away from the base lens of the eye protector. The wearer can thus peel away the tear-off layers of the stack, one by one, by grasping the opposing tab (the tab opposite the retention mechanism), and pulling the tear-off layer across the eye protector toward the retention mechanism. The tension from the wound loop of the tab around the retention mechanism helps keep the released tear-off layer on the side of the eye protector. A tacky surface of a capturer (e.g., a sticky pad or piece of tape), or the back side of a previously removed and captured tear-off layer helps hold the released tear-off layer to the side of the eye protector, and out of the viewing area of the wearer.

DETAILED DESCRIPTION

Figure 1:
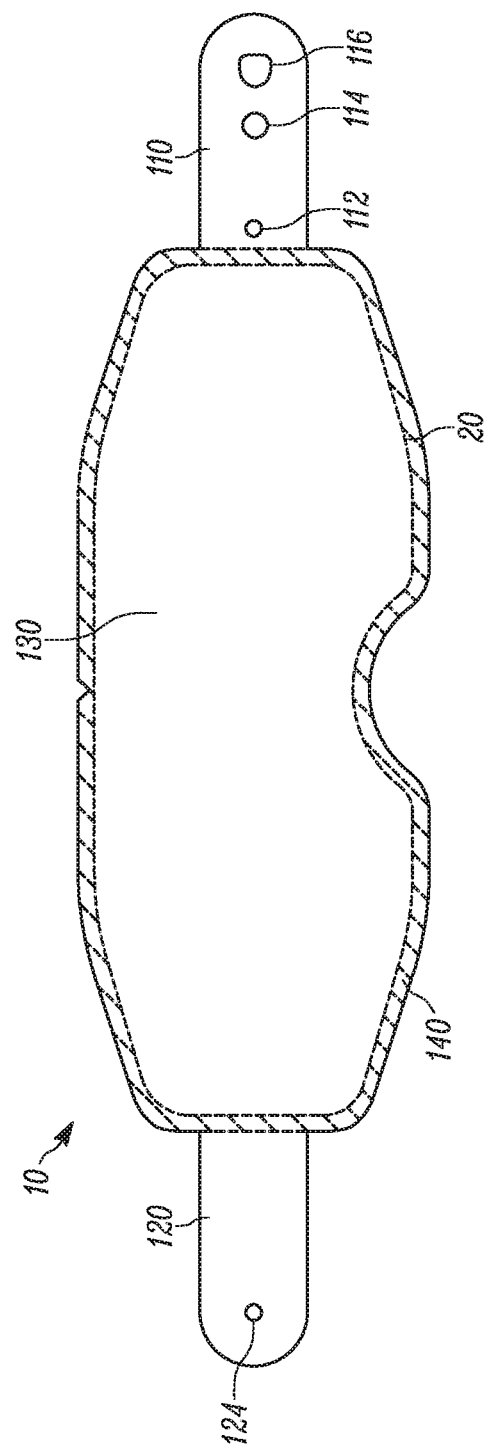
FIG. 1 shows an example of a laminated tear-off lens stack in accordance with embodiments described herein.

The present disclosure describes examples of a tear-off lens system that facilitates capture of removed lenses. The described systems allow a user to tear-away lenses to help keep the field of vision clear, without contributing to the litter and other problems associated with tear-off lenses.

It has proved challenging to develop techniques and systems that offer the benefits of tear-off lenses without contributing to the disposal and litter problems associated with tearoffs. Some approaches seek to use a "roll off" system, whereby a single layer of film is disposed between two rotating spools that are placed on opposing edges of an eye protector. As the film layer becomes soiled, a user can attempt to clear the field of view by advancing the film from one spool to the next.

Because the soiled portion of film in a roll off system is rolled within a second spool, such a system does not face the litter issues of a tear-off system, as there is no discarded layers to dispose of. However, the roll off system has many shortcomings that make the system less desirable for many applications. For example, unlike a tear-off system, a roll off system can only offer a protector that has a flat, linear shape because the width of the rolling film must be able to fit to roll off of a first spool and onto a second spool. Accordingly, for viewing surfaces with non-linear shapes—such as goggles that have an arch for a wearer's nose—a roll-off system will be unable to clean the entire field of view. Indeed, a roll off system can only clean a viewing lane as wide as the narrowest portion of the eye protector lens. A tear-off system, on the other hand, can be configured to fit precisely (or nearly precisely) over the entire eye protector, regardless of shape, thereby producing a clear view over the entire field of vision with each torn-off layer.

Another shortcoming of roll off systems is that the advancing layer must be able to freely slide across the surface of the eye protector. As a result, the rolling layer cannot adhere or attach to the layer. This allows for debris and other un-removable vision occluding material to become disposed between the protector base layer and the advancing roller layer. Moreover, advancing the layer creates friction on the base layer of the protector, which can generate scratches and other damage to the base layer of the eye protector. Further, the advancing roller can result in smudging, smearing or other undesirable vision occluding effects. A tear-off system, however, can be configured to attach, adhere, or otherwise seal with the base lens of the eye protector. This inhibits un-removable material from situating between the tear-off stack and the base lens, and also avoids scratching caused by an advancing roller film.

Yet another shortcoming of the roll off system is the complicated mechanical structure of the roller. Each roller of the spool must be configured to advance film from one spool to the other, which involves a complicated mechanical interaction between the two spools. This complicated mechanical interaction provides many potential modes of failure that can be debilitating to a wearer if the failure occurs at an inopportune time. For example, one spool or canister can jam with mud or debris, thereby causing failure at inopportune times. Tear-off systems, on the other hand, do not involve complex mechanical equipment, and therefore have less potential modes of failure. Accordingly, the tear-off systems are simpler to use and operate, less expensive, and more reliable than the roll off systems.

The present disclosure presents examples of a tear-off system that addresses some or even all of the above-described shortcomings of the roll off system, while also addressing the disposal/littering issue present among other tear-off systems. The present disclosure therefore describes laminated stacks, eye protectors, and related systems that facilitate the capture and/or collection of released tear-offs so that the torn off layers are not tossed or discarded as undesirable litter.

Some embodiments of the presently described tear-off capture system, or a kit for making such a tear-off capture system, include an eye protector and a lens stack that can mount on the eye protector. The eye protector includes a retention mechanism, and in some examples, a capturer. Upon mounting the lens stack to the eye protector, a wearer can tear away individual layers of the lens stack, and the retention mechanism (in some examples, with the assistance of the capturer and/or other previously torn away layers of the stack) maintains or holds the torn away layer with the eye protector, away from the wearer's field of vision.

Examples of the eye protector can include goggles, a visor, a helmet, glasses (e.g., sunglasses or safety glasses), a face shield, masks, or the like. The eye protector includes a base lens layer that protects a wearer's eyes (or other portions of the wearer's face and head) from projectiles, debris, fluids, wind, etc. The base layer can be flexible or rigid depending on the intended use of the application. The eye protector also includes a support mechanism that helps hold the eye protector onto the wearer (e.g., onto the wearer's head). The support mechanism can include a strap or band (e.g., for goggles), a helmet, hat, hood, or other head covering device (e.g., for a visor or face shield), extended arms (e.g., for glasses or safety glasses), or the like.

In some forms, the eye protector also includes a retention mechanism. The retention mechanism mounts to a portion of the eye protector, for example, to an edge or frame of a goggle, visor, or face mask. Certain aspects of the retention mechanism include a buckle configuration. The buckle configuration includes a slot or channel configured to receive a tab of the lens stack. In some examples, the retention mechanism also includes a holding structure, such as a pin, hook, finger, clip, ball, joint, or the like. In this manner the retention mechanism can serve as a hinge about which the tear-off layers of the lens stack pivot upon removal.

The retention mechanism can be a component of the eye protector, or it can be an add-on component, configured to be added to pre-existing eye protectors. For example, some eye protectors can be provided with a retention mechanism on the eye protector itself (e.g., built in to the frame of a goggle or helmet, etc.). In other embodiments, the retention mechanism can be configured to clip, adhere, snap, or otherwise attach to a pre-existing eye protector.

So configured, an eye protector with a retention mechanism operates in connection with a tear-off lens stack with a corresponding tab so that the tear-off layers are retained with, or captured by, the eye protector as they are released from the stack, rather than being immediately discarded. In some examples, the retention mechanism is mounted on and/or mountable to the eye protector at an angle. The angle can be configured to facilitate the unwinding of released tear-off layers around the eye protector. For example, the retention mechanism can have a surface that is angled away from the surface of the base lens layer so that the surface applies tension to the tear-off layers of the lens stack.

By some approaches, the eye protector will employ a capturer that facilitates holding one or more released tear-off layers to the eye protector and/or the side of a wearer's head, away from the eye protector's field of view. The capturer can attach to, or be a part of, the eye protector and/or the support mechanism of the eye protector. The capturer may be referred to as a capturing device, a capturing mechanism, a grabber, a gripper, a holder, or by a similar name.

The capturer can include a tacky surface or a tacky pad on one side of the eye protector to assist holding and/or capturing a tear-off lens that has been released from the lens stack. The capturer can also include a gate, a pin, a magnet, a fastener, a suction device, or the like. In some aspects, the capturer can include an adhesive spray applied to the side of the eye protector (e.g., to a strap of a goggle, or to a side of a helmet). In particular, the capturer facilitates capturing the first (or upper-most) tear-off lens from after it has been released (e.g., torn off or peeled away) from the lens stack.

Depending on the application and intended use, some examples may not employ a capturer, as wind and other forces may be sufficient to hold the released layers against the side of the eye protector or the wearer's head. For example in certain racing environments, the wind in the face of the wearer may be sufficient to hold the released tear-off layers against the side of the wearer's head even without the use of a capturer. However, even in these embodiments, the capturer can be employed to inhibit the torn away layers from flapping in the wind.

Certain embodiments described herein also relate to stacks of tear-off lenses. The tear-off stacks can be used in connection with the eye protectors described herein. In some examples, the tear-off stacks can be components of a kit and/or a system that includes the eye protectors and retention mechanisms described herein.

In some examples, a stack of tear-off lenses includes a plurality of releasable lenses. The stack may be laminated together, for example, with an adhesive. The lens stack has a central viewing area that is configured to generally cover the base lens layer, and two tabs that each extend from opposing edges of a central viewing area (e.g., a first edge on the right side and a second edge on the left side) of the stack. In some examples, only the central viewing area is laminated with an adhesive, such that the opposing first and second tabs are not laminated together, and are thus separable. That is, lens stack may only be laminated along a middle portion of the stack, so that the adhesive is only applied between first and second edges of the central viewing area.

In operation, a wearer can remove the upper-most layer of a tear-off stack by grasping the first tab on the first side of the eye protector and pulling the tear-off layer across the eye protector toward the second side of the eye protector. The first released layer will be tensioned and/or biased toward the second side of the eye protector, whereby a capturer (e.g., a tacky surface) helps to hold the released tear-off layer to the side of the eye protector and/or the wearer's head. In this position, the captured tear-off layer will thus present the inward surface—which comprises the laminated adhesive layer—to face outwardly, thereby providing a tacky surface by which the next released tear-off layer will come into contact. Through this tacky surface, the next released tear-off layer will hold to the eye protector and/or wearer's head, while also exposing yet another tacky surface. This process can be repeated for as many tear-off layers exist on the stack (or stacks) mounted to the eye protector.

In some examples, the lower-most layer of the lens stack (also referred to as the inward or inward-most layer, the bottom layer, etc.) includes an adhesive layer applied to a lower surface. The adhesive layer is configured to attach and/or adhere the lens stack to the base layer of the eye protector. This adhesive layer can be applied to all, or to a portion of the lower surface of the lower-most layer. For example, the adhesive layer can be applied to the perimeter edge of the layer (e.g., as described in the above referenced U.S. Pat. No. 6,536,045) so that a majority of the central viewing area of the lens stack remains un-adhered to the base layer. This peripheral seal configuration can help reduce bubbles and other objects that may result in optical artifacts affecting viewability through the eye protector/lens stack combination.

In other examples, adhesive can be applied to a majority, or even the entire lower surface of the lower-most layer of the lens stack. For example, certain embodiments may employ a dry-mount (e.g., a self-wetting) adhesive to the lower-most layer as (e.g., as described in the above referenced U.S. patent application Ser. No. 14/307,189), to facilitate adhering the lens stack to the base layer while inhibiting the formation of bubbles and other optical artifacts that impair visibility.

The adhesive applied to the lower surface of the lens layer can be configured so that the peel strength required to remove the lower-most layer from the base layer is higher than the peel strength required to remove the tear-off layers from the stack. In this manner, a wearer can remove each layer of the stack without causing the stack itself to delaminate from the base layer of the eye protector. In embodiments that employ the peripheral seal on the lower-most layer, the total surface area of the adhesive adhering the stack to the base lens will be less than the surface area adhering each tear-off lens to the stack, thus the tack of the peripheral adhesive layer may be sufficiently higher than the tack between each of the tear-offs. In some examples, the adhesive on the lower surface is configured to remain attached to the lower-most lens layer of the stack, even after it is removed from the eye protector. In this manner, the lens stack can be removed from the eye protector without having vision occluding adhesive residue remaining on the eye protector lens. This allows the lens stack to operate as a replaceable stack.

By employing an adhesive on the lower surface of the stack, the stack can adhere to the base lens without the use of pins or other mounting mechanisms on the base lens. This can provide the added benefit of allowing a base lens to be pin and hole free, which can significantly increase the structural integrity of the lens, thereby improving the safety properties of the eye protector. This can be particularly beneficial in environments where exposure to high speed projectiles is high, such as racing environments, military environments, and in workshops that employ power tools.

The adhesive mounting capabilities of the laminated stack also allow for a sealing engagement between the stack and the base lens of the eye protector. In this manner, the sealed engagement inhibits or even prevents fluids, debris, and other material from entering the space between the base lens and the stack.

Some examples provide for multiple stacks to be mounted on top of one another, so that additional tear-offs can be placed on an eye protector at a given time. This can be particularly useful in situations where a wearer expects to wear the eye protector for an extended period (or in situations where the wearer anticipates removing tear-offs with high frequency without being able to add or adjust the eye protector. In such a situation, each stack can be laminated and/or adhered to the stack below it before installation onto the eye protector. In this manner, the lower-most layer of one stack, which may be tables, will adhere to the upper-most layer of a lower stack, and will therefore tear away along with that upper-most layer when removed by a wearer.

The figures included with this application show in greater detail various features, components, and configurations of lens stacks in accordance with the present disclosure. FIG. 1 shows an example of a laminated tear-off lens stack 10. The laminated tear-off lens stack 10 includes a plurality of releasable lens layers. The laminated tear-off lens stack 10 also includes a first tab 110 and a second tab 120 that extend from opposing sides or edges of a central viewing area 130. The first tab 110 includes multiple holes or cutouts 112, 114, 116 that facilitate grasping of the tabs and/or removal of the tear off layers. The first tab 110 is configured to interact with a first side 210 of an eye protector 200 and serves to provide a grasping portion to help the wearer grasp and release each layer of the lens stack 10. Thus, layers on the first tab 110 (the tab on the right side of the figure) can be arranged on the first side 210 (the right side) of the eye protector 200 in a manner that facilitates grasping and removal of the tabs. In this configuration, the wearer may grab the tabs on the left side of the wearer's face (i.e., the right side of the figure), and pull across their face to release, or tear-away, the top most layer.

The hole 112 on the first tab 110 is configured to interact with a pin 212 or other structure located on the first side 210 the eye protector 200. This interaction helps keep the lens stack 10 attached to the eye protector 200. In this embodiment, removal of an upper-most lens layer 20 causes a tab of a subsequent lens layer to extend laterally outward upon removal of a layer above it. In this manner, only the tab of an upper-most layer of a stack will extend outwards, thereby inhibiting a wearer from grasping a tab that would remove more than one layer (e.g., a tab of a layer that is not the upper-most layer). The configuration of the first tab 110 can take on different shapes, appearances, or configurations, depending on the application or use of the stack.

Figure 2:
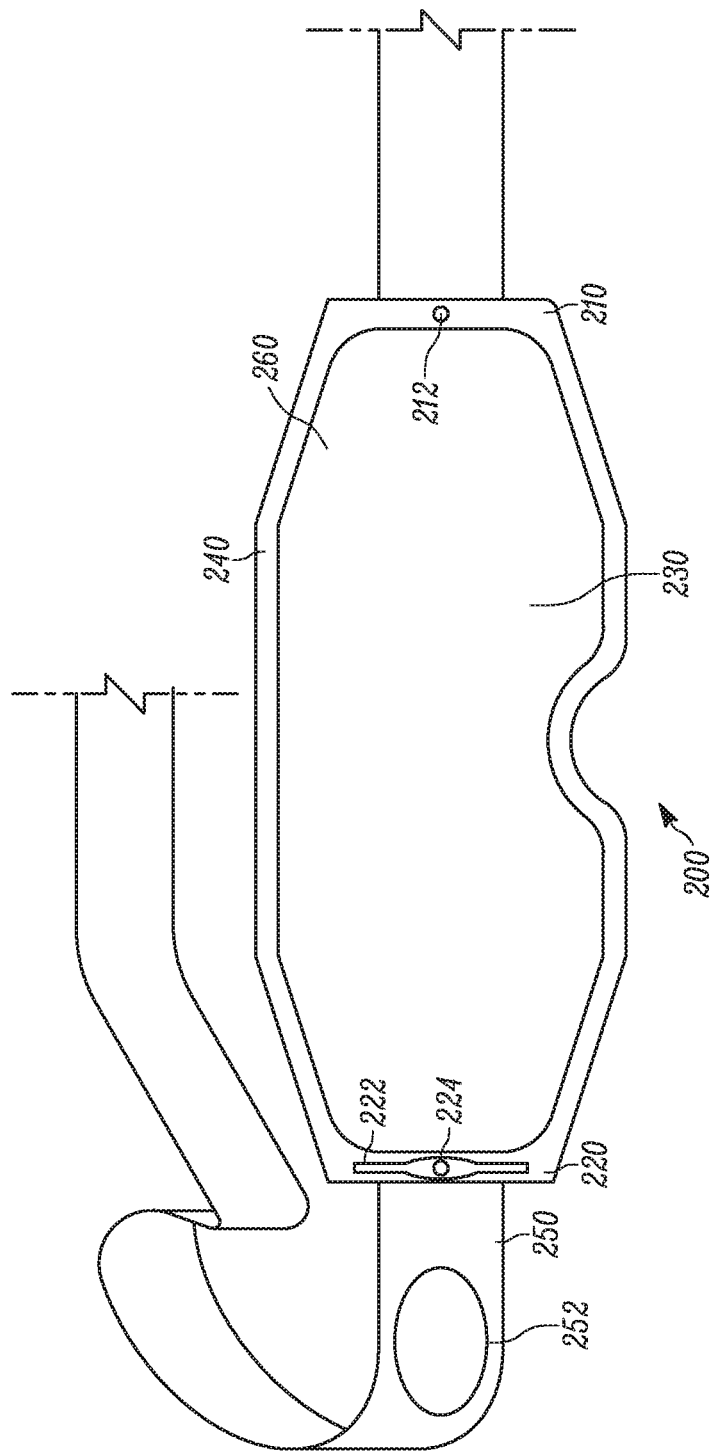
FIG. 2 shows an example eye protector in accordance with certain aspects of the present disclosure.

The second tab 120 is configured to operate in connection with a retention mechanism 222 mounted on the second side 220 of the eye protector 200. FIG. 2 shows an example of an eye protector 200 with a retention mechanism 222. The second tab 120 may also contain holes 124, cutouts, or other connection mechanisms that corresponds to the holding structure 224 on the retention mechanism 222. The second tab 120 is configured to be placed through a slot or channel 226 present on the retention mechanism 222. In this manner, the second tab 120 can be wound, wrapped, or looped around the retention mechanism 222 as it mounts to the eye protector 200 so that the loop creates tension tending to pull the tear-off lens layers away from the base lens 260 of the eye protector 200. In this configuration, the wound/wrapped second tab 120 serves as a spring-like hinge that provides tension or a curvature that biases the tear-off lens layers to remain away from the base lens 260 of the eye protector 200 after removal.

The hole 124 located on the second tab 120 can interact with the holding structure 224 located on the retention mechanism 222 to keep the lens stack 10 attached to the eye protector 200. For example, the hole 124 can interact with a pin or knob on the retention mechanism 222 so that the tab stays engaged with the retention mechanism upon winding thereon.

The central viewing area 130 located on the lens stack 10 enables the wearer to see through the multiple lens layers while using the lens stack 10. The shape, size, and/or configuration of the central viewing area 130 of the lens stack 10 may correspond to that of the central viewing area 230 of the eye protector 200. However, the central viewing area 130 can also be of a shape or size different than the eye protector 200. For example, the central viewing area 130 may be configured to have a shape or size that covers all or a portion of the base lens 260 of the eye protector 200, which can have a shape of goggles, a visor, helmet, glasses, face shield, or the like. In some forms, the central viewing area 130 is configured to cover a primary field of vision of a user wearing the eye protector.

In some examples, an adhesive layer 140 is located near the perimeter of the central viewing area 130. The adhesive layer 140 helps adhere the lower-most lens layer to the base lens 260 on the eye protector 200. In one embodiment, the adhesive layer 140 is present only on the perimeter of the central viewing area 130. Alternatively, the adhesive layer 140 may cover substantially all of the central viewing area 130.

In another example, the lens stack includes a protective layer on the inner surface of the lower-most lens layer located on the lens stack 10. This protective layer prevents the adhesive located on the inner surface of the lower-most layer from being compromised prior to installation. To engage the adhesive layer 140 located on the inner surface of the lower-most lens layer, the wearer may remove the protective layer.

In some examples, there is an intermediary adhesive located between each successive lens layer. Here, layers of the lens stack 10 are laminated together about the central viewing area 130 in a manner that allows each layer to be peeled away from the stack from the first tab 110 towards the second tab 120. The lamination may be such that no adhesive is applied between the tear-off layers along the tabs. That is, the lens stack 10 may be laminated such that the intermediary adhesive extends only between opposing edges of the central viewing area 130 of the lens stack 10. This allows the adhesive free tabs to be sufficiently flexible to wind around a retention mechanism 222 or be arranged to facilitate the release of a top-most gripping tab as explained above. The lamination may also be applied such that the adhesive layer remains with the torn-off layer so that the adhesive is outwardly exposed as the lens layer is held against the eye protector 200 (e.g., on the capturer). In this manner a tacky surface on the outwardly exposed layer can serve to help collect and capture each subsequently removed lens layer.

In some aspects, the lens stack 10 is laminated with an adhesive such that the refractive index (i.e., index of refraction) of the adhesive matches the refractive index of the tear-off layers within about 0.2. So configuring the refractive indices of these layers minimizes the reflection of light passing through the lens stack 10, thereby improving the viewability through the lens stack 10. The tear-off lenses of the lens stack 10 and the laminating adhesive are generally transparent and/or optically clear. In some examples, the tear-off layers and adhesive can include any of the films and/or adhesives described in U.S. Pat. Nos. 6,388,813, and 6,536,045, and U.S. patent application Ser. No. 14/307,189, each of which are hereby incorporated by reference in their entireties. In some situations, some or all of the lenses of the stack may be equipped with a coating, such as an anti-glare coating, an anti-reflection coating, an anti-fog coating, a scratch-resistant coating, or a water-resistant/wicking coating.

As used herein, the term transparent refers to a material that allows light to pass through so that objects behind the material can be seen by a user. While many embodiments refer to the term transparent to refer to material that is relatively clear or un-occluded, it is considered that in some aspects, the term transparent can apply to some material that is translucent or partially occluded. The term transparent can also refer to material that is colored, tinted, etched, hazed, patterned, etc., provided that at least some light passing through is sufficient to allow objects behind the material to be seen.

In some approaches, while the central viewing area 130 of the stack will be laminated with adhesive, both tab portions will be un-laminated. That is, in such embodiments, no adhesive will exist between each layer of the stack at the tabs (or at least across a portion of the tabs). Such a configuration will allow the tabs on a first side (e.g., a grasping side) to be distinguished and separated, thereby facilitating a wearer to quickly remove a tear-off layer. Moreover, by eliminating adhesive/lamination on the second tab 120 (e.g., the retention mechanism engaging tab), the tab will have more flexibility so as to wind around the retention mechanism 222. In some examples, depending on the structure of the retention mechanism 222, the second/retention tab 120 may have some adhesive to facilitate engagement with the retention mechanism 222, and to help provide added tension when applied to the eye protector 200. In other examples, however, the second/retention 120 tab will have no adhesive whatsoever.

In some aspects, the tear-off lenses are laminated together so that the upper (or outer) surface of the recently exposed layer is generally un-tacky. That is, the stack can be configured so that the adhesive layer between the film layers generally remains on the lower (or inward) surface of the released tear-off layer. In this manner, the lower surface of the released layer will have a generally tacky surface, which can facilitate holding and capturing of a subsequently released layer.

FIG. 2 shows an example of an eye protector 200 to which the lens stack 10 can be attached. The eye protector 200 has a first side 210 and a second side 220. On the first side 210 is a pin 212. The pin 212 is configured to interact with the holes 112, 116, or similar corresponding structure located on the first tab 110 of a lens stack 10. Contact between the pin 212 and holes 112, 116 helps the lens stack 10 stay attached to the eye protector 200 at a first side 210.

The second side 220 includes a retention mechanism 222. The retention mechanism 222 can be a component of the eye protector 200, or it can be an add-on component, configured to be added to pre-existing eye protectors. For example, some eye protectors can be provided with a retention mechanism 222 on the eye protector 200 itself (e.g., built in to the frame of a goggle or helmet, etc.). In other embodiments, the retention mechanism 222 can be configured to clip, adhere, snap, or otherwise attach to a pre-existing eye protector 200. Additionally, the angle of the retention mechanism 222 can be configured to facilitate the unwinding of released tear-off layers around the eye protector 200. For example, the retention mechanism 222 can have a surface that is angled away from the surface of the base lens 260 so that the surface applies tension to the tear-off layers of the lens stack 10.

Certain embodiments may employ additional and/or other techniques and components in connection with the retention mechanism 222 and the corresponding tab of the lens stack 10 to generate tension there between. Because the tension helps bias a released tear-off away from the lens, other tension generating components may be used to achieve a desired level of tension. Such components can include, but are not limited to, stretchable material in or on the tab or the retention mechanism 222, springs incorporated into the retention mechanism, shapes and configurations designed to utilize air flow to facilitate the released lens flapping toward the back of the wearer's head, etc.

The retention mechanism 222 includes a holding structure 224 which can help attach the second tab 120 to the retention mechanism 222. The holes or cutouts 124 located on the second tab 120 interact with the holding structure 224 on the retention mechanism 222 to attach the second tab 120 to the eye protector 200. The holding structure 224 engages the hole 124 located on the second tab 120. Thus, the holding structure 224 may take a variety of forms including a pin, ring, loop, hook, fastener, or the like.

The eye protector 200 also includes a base lens 260 and a central viewing area 230. The base lens 260 protects the wearer's eyes, or other portions of the face, from projectiles, debris, fluids, wind, and the like. The base lens 260 may have a large surface area that encompass all or a substantial portion of the central viewing area 230. Alternatively, the base lens 260 can have a smaller surface area than the central viewing area 230. In some embodiments, the perimeter of the central viewing area 230 is coextensive with the perimeter of the base lens 260. The shape of the base lens 260 can be defined by a perimeter 240 of the eye protector 200. The perimeter 240 can be composed of a rigid material. Alternatively, the perimeter 240 can be a flexible or moldable material. The perimeter can also serve as the attachment surface for the retention mechanism 222 on the second side 220 and the pin 212 on the first side 210. In another embodiment, there is no perimeter surrounding the base lens 260. Here, the retention mechanism 222 and pin 212 can be attached to another surface on the eye protector 200. Alternatively, the retention mechanism 222 and pin 212 may be located on a support mechanism 250 of the eye protector 200. The support mechanism 250 may be a strap, band, helmet, hat, hood, or any other head or face covering device, or extended arms like those found on glasses. The support mechanism 250 helps maintain the eye protector 200 on the head or face of the wearer. The support mechanism 250 may also help retain a discarded lens layer such that it is out of wearer's field of vision.

In some embodiments, the support mechanism 250 may include a capturer 252. The capturer 252 is configured to interact with the upper-most lens layer 20 of the lens stack 10. Upon release of the upper-most lens layer 20, the tension created by wrapping the second tab 120 around the retention mechanism 222 biases the upper-most lens layer 20 toward the capturer 252 and out of the wearer's field of vision. In some embodiments the capturer 252 is integrated into the support mechanism 250. Alternatively, the capturer 252 can be an additional component attached to the support mechanism 250 by the wearer. For example, the capturer 252 can include a gate, a clip, a suction device, a fastener, or the like. Additionally, the capturer 252 can be composed of a material different than that of the support mechanism 250. The capturer 252 may be tackier or may include an adhesive in order to assist in capture and retention of the upper-most lens layer 20. The tacky surface can be applied, for instance, by spraying an adhesive on the support mechanism 250, or by applying an adhesive pad, ribbon, or tape to the support mechanism 250. In other examples, the support mechanism 250 does not include a capturer 252. Instead, the wind or another force is sufficient to bias the upper-most lens layer 20 against the support mechanism 250.

Figure 3A:
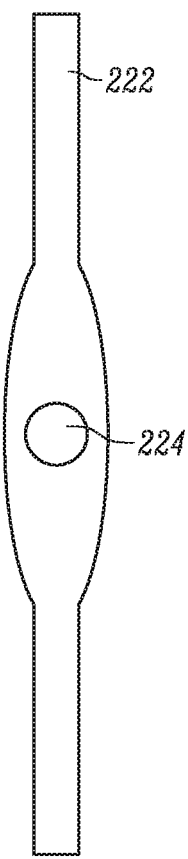
FIGS. 3A and 3B show front and side views, respectively, of a retention mechanism that can be used in conjunction with an eye protector, as described herein.

FIG. 3A shows one configuration of the retention mechanism 222. Here, the retention mechanism 222 is in a buckle-type configuration. In some examples, the retention mechanism 222 can include an adhesive element, pin, ring, or other element. The retention mechanism 222 can be located on a second side 220 of an eye protector either as an integrated component or add on piece. Additionally, the retention mechanism 222 can contain a holding structure 224. The holding structure 224 may be in the form of a pin, ring, loop, hook, fastener, or the like. The holding structure 224 interacts with a hole 124 of a second tab 120. In some embodiments, the holding structure 224 is a pin protruding outward from the outer most surface of the retention mechanism 222. The hole 124 located on the second tab 120 is configured to fit over the holding structure 224 and thereby securely attach a plurality of lens layers or lens stack 10 to the eye protector 200.

Figure 3B:
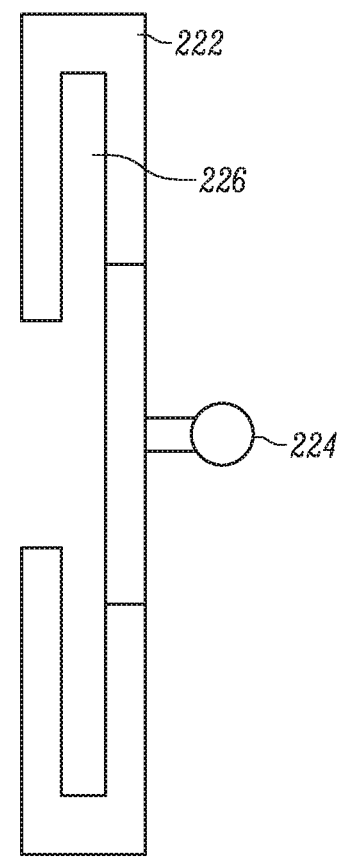

FIG. 3B shows another angle of the retention mechanism 222. In this embodiment, the holding structure 224 is seen protruding from the outer most surface of the retention mechanism 222. Additionally, a slot or channel 226 is shown between two faces of the retention mechanism 222. The second tab 120 is configured to pass through the slot or channel 226 of retention mechanism 222. Then second tab 120 is next wrapped around the retention mechanism 222 and the hole 124 aligned with the holding structure 224. The hole 124 located on a second tab 120 interacts with a holding structure 224 protruding from the outer most surface of a retention mechanism 222. The width of the slot 226 may be defined by two inner surfaces of a retention mechanism 222. In some examples, the width of the slot can change to encompass a plurality of lens stacks 10. In other examples, the width of the slot is fixed. In still other examples, the retention mechanism 222 may be composed of flexible material to allow for separate additional lens stacks 10 to pass through the slot 226. In some forms, the width of the slot 226 can be manually manipulated by a sliding mechanism.

Figure 4:
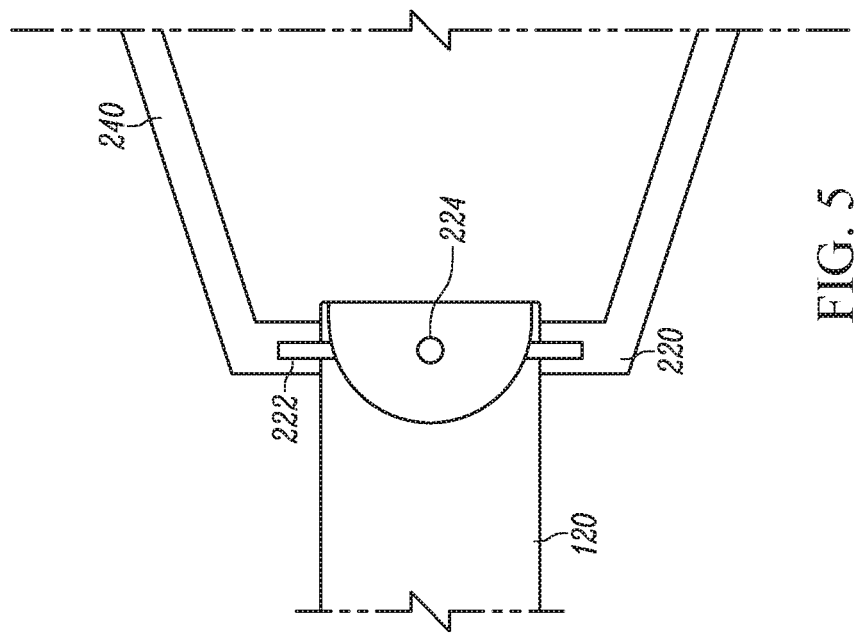
FIG. 4 shows a lens stack tab inserted through a retention mechanism, as a step in the installation of a laminated tear-off lens stack, in accordance with aspects described herein.

FIG. 4 shows a second tab 120 of a lens stack 10 interacting with a retention mechanism 222 of an eye protector 200 during an exemplary installation and/or use of the presently disclosed technology. In this embodiment, the second tab 120 (i.e., the tab shown in the left in the figure) will slide through a slot 226 in the retention mechanism 222, inserting from the left side of the image to the right so that the inserted tab extends over the base lens 260 of the eye protector 200, and so that the central viewing area 130 and the first tab 110 of the lens stack 10 extend away from (to the left) of the eye protector 200.

Figure 5:
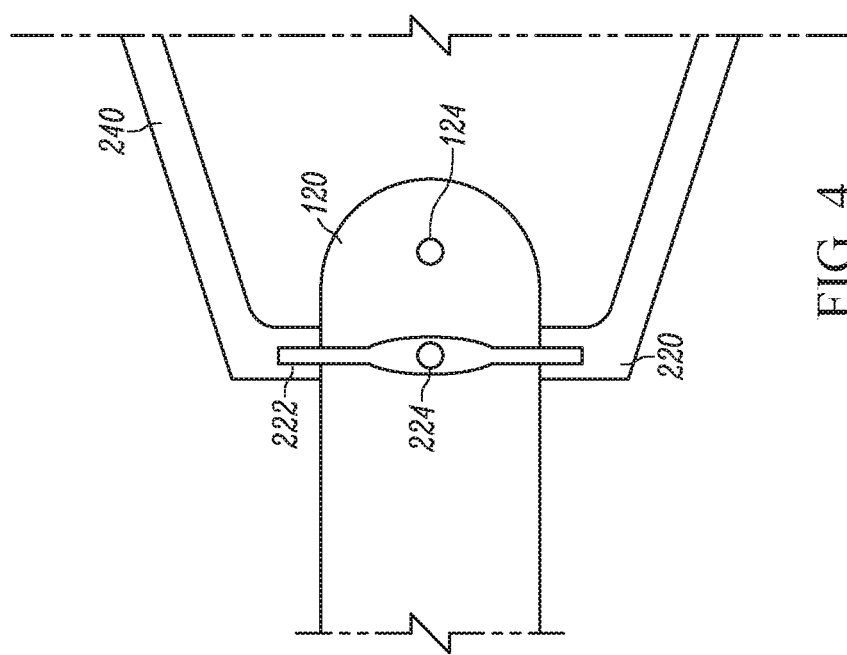
FIG. 5 shows a lens stack folded over a retention mechanism, as a step in the installation of a laminated tear-off lens stack, in accordance with the aspects described herein.

FIG. 5 shows another example step in the installation and/or use of the lens stack 10. In this embodiment, after inserting the second tab 120 through the slot 226 of the retention mechanism 222, the second tab 120 is folded over the outer most surface of the retention mechanism 222. The hole 124 located on the second tab 120 can then be aligned with the holding structure 224 protruding from the outer most surface of a retention mechanism 222. The interaction between the holding structure 224 and hole 124 on the second tab 120 holds the second tab 120 in place on the eye protector 200.

Figure 6:
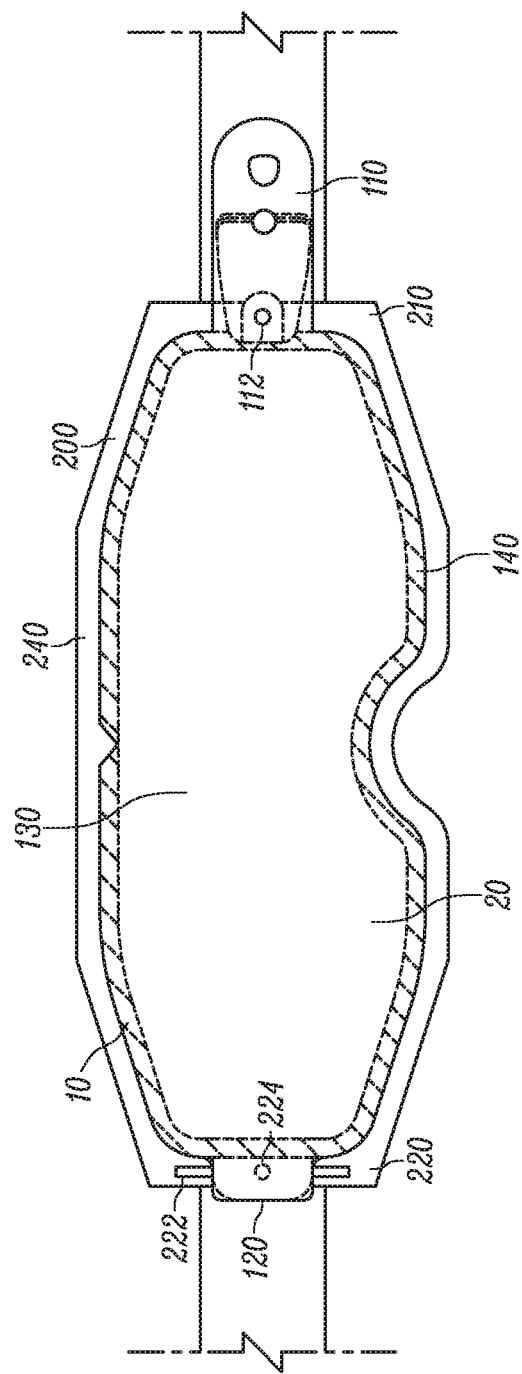
FIG. 6 shows a laminated tear-off lens stack installed on an eye protector, in accordance with aspects described herein.

FIG. 6 shows the lens stack 10 attached to the eye protector 200. After the second tab 120 is attached to the retention mechanism 222 of the eye protector 200, the wearer pulls the lens stack 10 across the base lens 260 and towards the other side of the eye protector 200. This creates tension between the lens stacks 10 at the location of the second tab 120 and biases the plurality of lens layers toward the support mechanism 250 and capturer 252.

An adhesive layer 140 located on the inward facing surface of the lower-most lens layer is aligned with the perimeter 240 of the base lens 260 of the eye protector. This adhesive layer 140 may cover all, a substantial portion, or the perimeter of the base lens 260. The adhesive layer 140 of the lens stack 10 is then secured against the base lens 260 of the eye protector 200. In one embodiment, the adhesive layer 140 is configured so that the peel strength required to remove the lower-most lens layer is greater than the peel strength required to remove lens layers in the lens stack 10. Alternatively, the lower-most layer of the stack may not include tabs. By not having tabs, the stack inhibits the unwanted or accidental removal of the lowest protective layer from the base layer of the eye protector. Thus, in situations where all the tear-offs have been removed, the system will still include one final layer that protects the integrity of the base lens.

The lens stack 10 contains a plurality of lens layers. Thus, there are several first tabs 110 coextensive with each other in the lens stack 10. The upper-most lens layer 20 is the first layer to be removed while the device is in use by the wearer. To facilitate the removal of one lens layer at a time, the first tabs 110 of the lens layers, excluding the first tab of the upper-most lens layer, are folded backward, over themselves to align the lateral-most hole 116, located on the first tabs 110, with the pin 212, located on the eye protector 200.

To remove a soiled layer, the wearer engages the extended first tab 110 and pulls the first tab 110 of the lens layer across the field of view, towards the second tab 120. In some configurations, upon detaching from the first tab 110 from the first side 210 of the eye protector 200, the first tab 120 of the lens layer immediately succeeding the recently released lens layer 20 will detach from the pin 212. The first tab 110 of the next lens layer is now in an extended formation and capable of being grasped by the wearer. This configuration enables the wearer to remove only the upper-most lens layer 20 when using the device.

Figure 7:
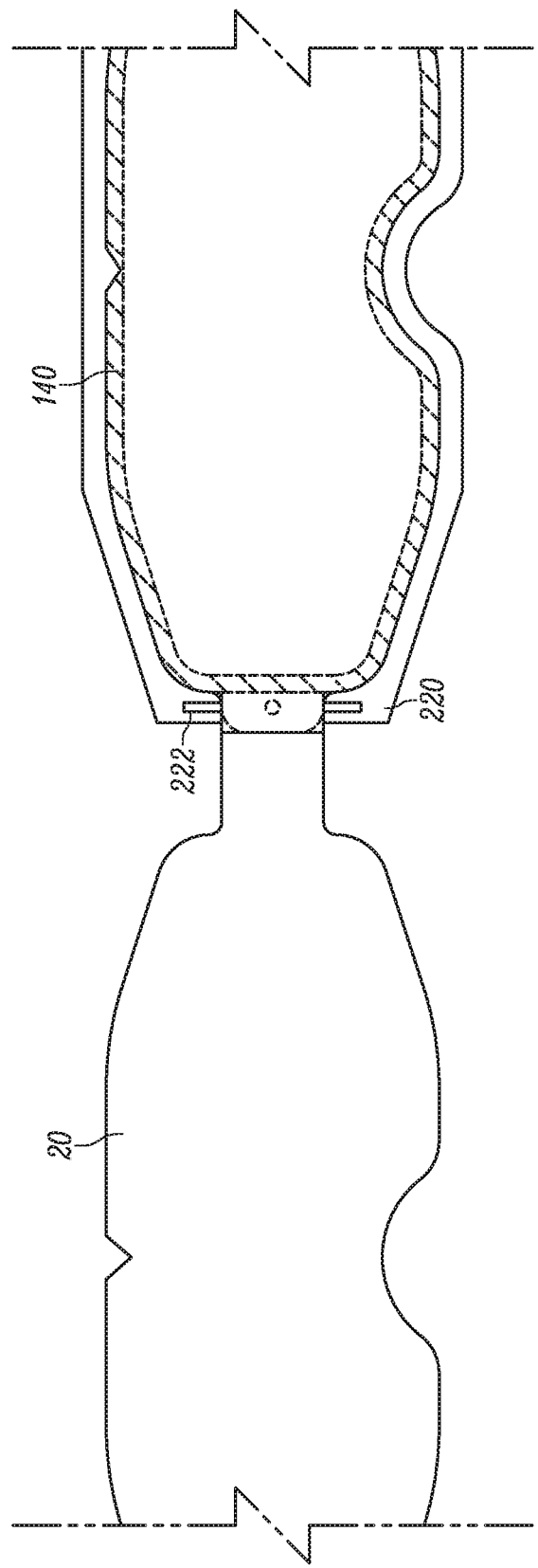
FIG. 7 shows a discarded layer of a laminated tear-off lens stack attached to an eye protector, in accordance with embodiments of the present disclosure.

FIG. 7 shows a discarded upper-most lens layer 20 of a lens stack 10. As described with respect to FIG. 6, when the second tab 120 is attached to the retention mechanism 222 via a holding structure 224, and the lens stack 10 is adhered to the base lens 260, the second tab 120 and therefore the lens stack 10 itself are placed in tension. This tension biases each layer of the lens stack 10 toward the support mechanism 250 and capturer 252. Consequently, even after release of the upper-most lens layer 20, the remaining lens layers in the lens stack 10 are still in tension and will be biased towards the support mechanism 250 and capturer 252 when the wearer engages their respective first tab 120. Additionally, the adhesive located on the inner surface of each lens layer provides a secondary method of attachment for a discarded lens layer. In some examples, a first upper-most discarded lens layer is secured to the support mechanism 250 via a capturer 252. This discarded lens layer contains an intermediary adhesive layer on its inner surface. In the lens stack 10, this adhesive layer helps attach that lens layer to a subsequently removed lens layer located after it in the lens stack 10. However, when a lens layer is discarded by the wearer, the intermediary adhesive layer located on the inner surface attaches to the outer surface of a subsequently discarded lens layer. This functionality can be repeated for each additionally discarded lens layer within a lens stack 10.

As described, the tear-off lenses can be laminated together so that the upper (or outer) surface of the recently exposed layer is generally un-tacky. That is, the stack can be configured so that the adhesive layer between the film layers generally remains on the lower (or inward) surface of the released tear-off layer. In this manner, the lower surface of the released layer will have a generally tacky surface, which can facilitate holding and capturing of a subsequently released layer.

Figure 8:
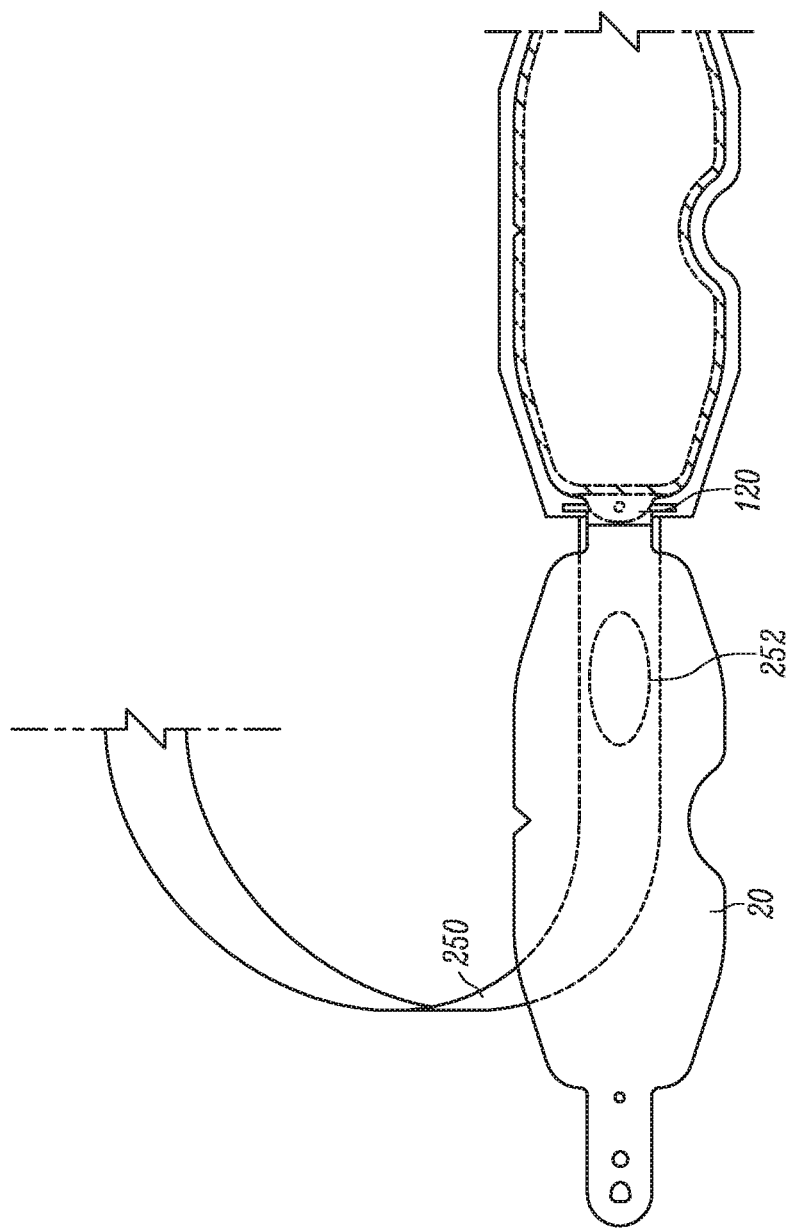
FIG. 8 shows a discarded layer of a laminated tear-off lens stack captured by a capture mechanism, in accordance with examples described herein.

FIG. 8 shows an upper-most lens layer 20 held by the capturer 252 located on the support mechanism 250. The capturer 252 is configured to help keep discarded lens layers, including the upper-most lens layer 20, out of the field of vision of the wearer. In one embodiment, the capturer 252 is an integral component of the support mechanism 250. In another embodiment, the capturer 252 is an additional component that is attached to the support mechanism 250 via a pin, heat, adhesive, or the like. The capturer 252 may optionally contain a tacky surface such as a sticky pad or tape. In another embodiment, the capturer 252 is an adhesive spray applied to the side of the eye protector 200 or support mechanism 250. In some examples the capturer can include other capturing equipment such as suction devices, clips, gates, pins, fasteners (e.g., hook and loop fasteners), or magnets.

Depending on the application and intended use, some examples may not employ a capturer 252, as wind and other forces may be sufficient to hold the released layers against the side of the eye protector or the wearer's head. For example in certain racing environments, the wind in the face of the wearer may be sufficient to hold the released tear-offs against the side of the wearer's head even without the use of a capturer. In this configuration, the subsequent layers are held in place by way of the adhesive (and in some cases, static), on the outwardly facing surfaces of the previously removed tear-off layers. However, even in these embodiments, the capturer can be employed to inhibit the torn away layers from flapping in the wind.

Figure 9:
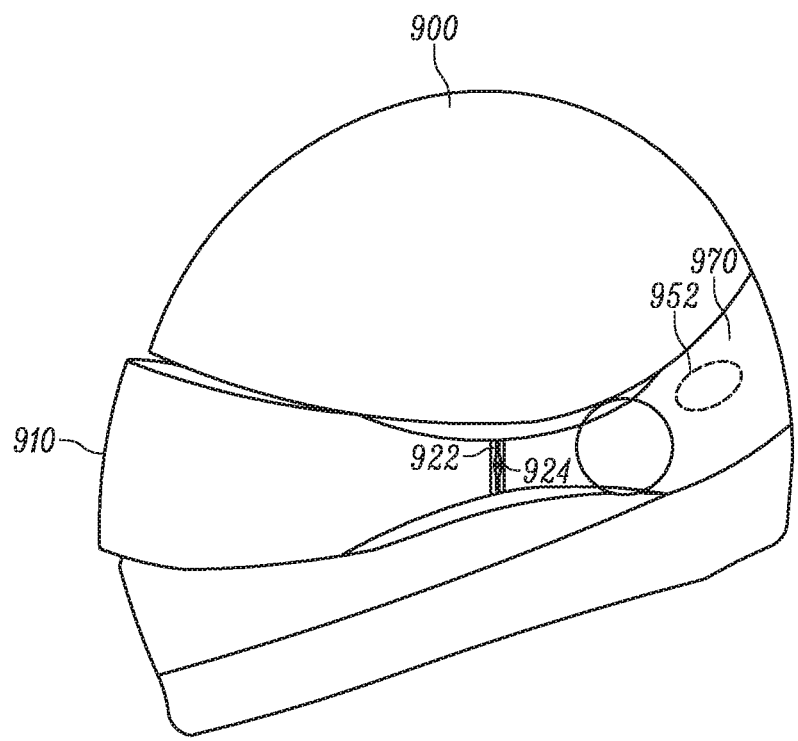
FIG. 9 shows a laminated tear-off lens stack on a helmet/visor type of eye protector, in accordance with certain aspects of the present disclosure.

The examples described above primarily relate to an eye protector that includes a goggle type configuration. The presently disclosed stacks and systems can be used with a variety of other eye protectors. For example, stacks can be configured to operate with glasses, safety glasses, face masks, face shields, windshields, windows, helmets, visors, or other similar devices. FIG. 9 shows one example of the lens stack 910 on an eye protector 900, where the eye protector 900 is in the form of a helmet/visor configuration. In this embodiment, the second tab 920 of the lens stack 910 is attached to a retention mechanism 922 via a holding structure 924. Additionally as shown, the upper-most lens layer 970 is discarded and attached to the side of the helmet/visor configuration by a capturer 952 (here, a tacky strip) applied to the side of the helmet/visor configuration. Optionally, the upper-most layer can be attached via a capturer 952 located on the support mechanism. The support mechanism 950, in this embodiment, can be the back of the helmet or the helmet itself. Alternatively, the support mechanism 950 can be a band, strap, or the like.

The present disclosure also provides methods of making, installing, and using the capture systems described herein, and the related components. For example, one method involves laminating a plurality of film layers together into a sheet formed by multiple lanes, such that some lanes remain laminated with an adhesive (wet), while other lanes remain un-laminated (dry), with little or no adhesive there between.

Figure 10:
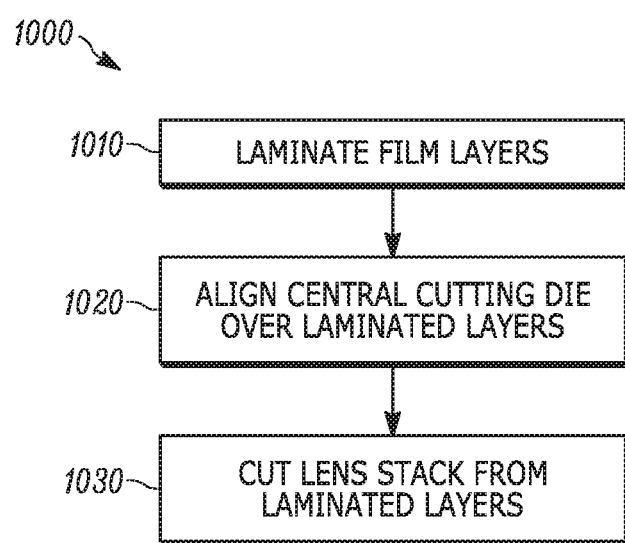
FIG. 10 is a flow diagram of a method of manufacture for a laminated tear-off lens stack, in accordance with examples of the present disclosure.

FIG. 10 is a flow diagram of an example method 1000 of manufacture of the lens stack 10. The steps include aligning a plurality of layers to be laminated together, laminating 1010 the layers, aligning 1020 the cutting die, and cutting 1030 the laminated layers to form a lens stack. The lens stack die cut can be configured so that the central viewing area of a lens stack is cut from a laminated lane (e.g., a "wet" lane) on a sheet or roll of material, whereas the tab portions are cut from un-laminated lanes (e.g., a "dry" lane) on the sheet or roll. Such an alignment allows the wet lane to cover all of the width of the central viewing area, i.e., the opposing first and second edges of the wet lane correspond with the first and second edges of the central viewing area. Alternatively, the wet lane may cover a substantial portion, or less, of the central viewing area. For example, in one embodiment an adhesive (wet) lane is wide enough to extend over a portion of the second tab of the lens stacks. Alternatively, an adhesive (wet) lane may extend over the central viewing area of the stack, while leaving a majority or even the entirety of the tabs free of adhesive (i.e., dry).

From this laminated sheet, some examples of the described lens stacks can be formed. For example, the lens stacks can be cut so that the central viewing area corresponds to the laminated (wet) lanes, with the opposing tabs cut from the un-laminated (dry) lanes on opposing sides of the laminated lane. In this manner, the described lens stacks having a laminated central viewing area and un-laminated tabs extending from two sides of the central viewing area can be formed. The lens stacks can be cut from a die that cuts multiple stacks at a time. In some examples, the dies are configured to both cut out the lens stacks, and also to cut out shapes and patterns in the stacks themselves, including the tabs, holes, slots, and other features of the lens stacks.

Figure 11:
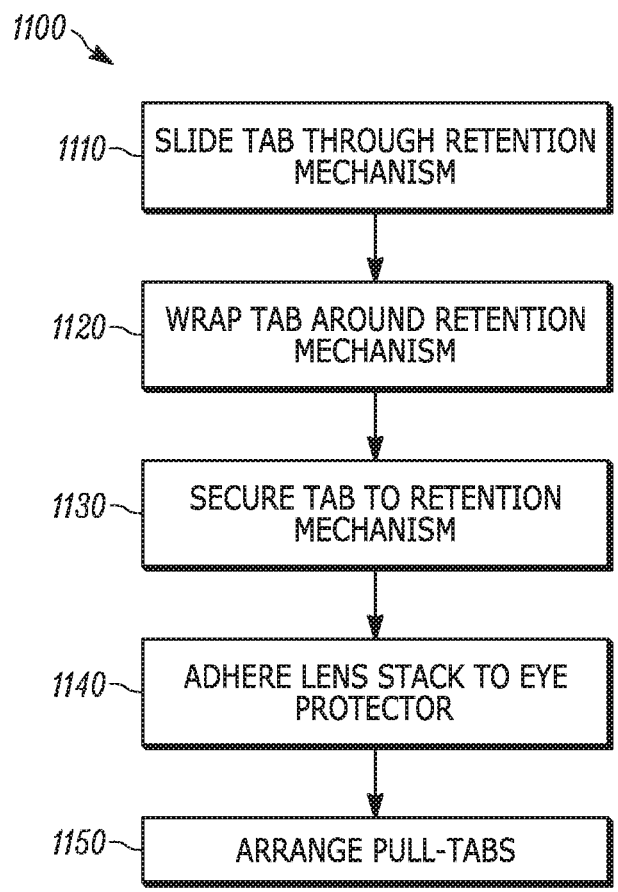
FIG. 11 is a flow diagram of an exemplary method of use and/or installation of a laminated tear-off lens stack, in accordance with the aspects described herein.

FIG. 11 is a flow diagram of an example method 1100 of using and/or installing a lens stack. Depending on the shape of the eye protector and base lens, installation and use of the lens stack may vary. In operation, the lens stack and the retention mechanism can interact by inserting 1100 the second tab through a slot in the retention mechanism so that the tab extends partially over the base lens of the eye protector and so that the central portion of the lens stack extends away from the side of the lens protector. The tab can then be hooked or otherwise connected to the retention mechanism by winding 1120 the inserted tab upwards and hooking 1130 a hole on the tab onto a pin, peg, or other holding structure on the retention mechanism to secure the tab. The lower-most layer of the lens stack is then adhered 1140 to the base lens via an adhesive layer. Lastly, the plurality of first tabs are arranged 1150 and secured to the pin to enable removal of one lens layer at a time.

Figure 12:
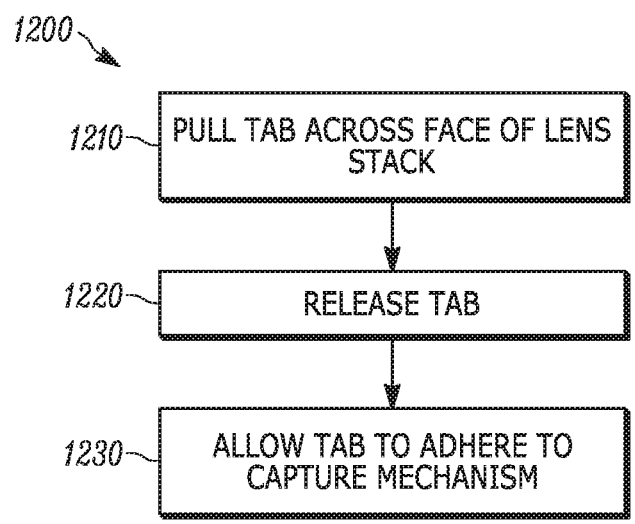
FIG. 12 is a flow diagram of a method of use of a laminated tear-off lens stack, in accordance with certain aspects of the present disclosure.

FIG. 12 depicts an example method 1200 of use of the lens stack. To remove the upper-most lens layer, a wearer can engage the first tab and pull 1210 it across the field of vision towards the second tab. The wearer can then release 1220 the first tab and allow the tension created at the retention mechanism to bias the recently released lens layer toward the capturer. The capturer then attaches 1230 to the released lens layer. This cycle can be repeated with each released lens layer. In some examples, methods 1000 and 1100 can be combined into one method of use. Such a combined method includes both the installation of the lens stack and the subsequent removal of the layers.

The present disclosure makes several references to an eye protector with a base lens that is protected by a stack of tear-off lenses. It should be noted that each reference to an eye protector can also refer to other protectable surfaces that are not necessarily intended to protect the eyes. For example, it is considered that the presently described capture systems and techniques can be employed in connection with cameras (e.g., video and still cameras), windows and/or windshields, screens and monitors (e.g., television screens, mobile device screens, etc.), clocks, watches, or the like. Moreover, some examples of the presently described capture systems can also be used with other surfaces that may be exposed to dirt, debris, fluids, or other spatter, including surfaces of vehicles (e.g., trains exposed to dirt or graffiti, the sides of vehicles, etc.), and buildings.

The present disclosure describes preferred embodiments and examples of a laminated tear-off capture system, and related components and methods of use and manufacture. Those skilled in the art will recognize that a wide variety of modifications, alterations, and combinations can be made with respect to the above described embodiments without departing from the scope of the invention as set forth in the claims, and that such modifications, alterations, and combinations are to be viewed as being within the ambit of the inventive concept. In addition, it should also be understood that features of one embodiment may be combined with features of other embodiments to provide yet other embodiments as desired. All references cited or discussed in the present disclosure are hereby incorporated by reference in their entirety.

The invention claimed is:

1. A tear-off lens capture system for use with an eye protector having a base lens and a frame supporting the base lens, the system comprising:
   a retainer configured to be mounted to an outward facing side of the frame so that the retainer extends away from the base lens, the retainer comprising:
      a peripheral wall configured to extend outwardly from the frame when installed on the eye protector, the peripheral wall defining a slot that is surrounded by the peripheral wall and the frame, the slot being positioned outward from the base lens when installed on the eye protector; and
      a holder protruding from the peripheral wall and extending away from the base lens when installed on the eye protector; and
   a lens stack configured to be mounted to an outward side of the eye protector, the lens stack formed of at least one releasable lens layer, the lens stack comprising:
      a central viewing area;
      a first tab extending from a first edge of the central viewing area; and
      a second tab extending from a second edge opposite the first edge of the central viewing area, the second tab having an end portion and an intermediate portion between the end portion and the central viewing area, the intermediate portion having a second tab width, and an aperture at the end portion;
   wherein the slot has a slot width that is at least as wide as the second tab width such that the intermediate portion of the second tab extends through the slot and at least partly around the holder, and wherein the aperture engages with the holder,
   wherein the lens stack comprises an upper lens layer and at least one intermediary layer, wherein the lens stack is configured so that each intermediary lens layer adheres to a previously released lens layer upon release from the lens stack while the second tab continues to be engaged with the holder.

2. The tear-off lens capture system of claim 1, wherein the second tab has a length configured to allow the second tab to be wound around at least a portion of the retainer so that the lens stack is placed in tension upon mounting to the eye protector.

3. The tear-off lens capture system of claim 1, wherein the lens stack comprises at least two releasable lens layers laminated together with an intermediary adhesive layer between each of the releasable lens layers.

4. The tear-off lens capture system of claim 3, wherein the intermediary adhesive layer extends between the opposing first and second edges of the central viewing area so that no intermediary adhesive layer is applied between the releasable lens layers along either the first or second tab.

5. The tear-off lens capture system of claim 3, wherein the intermediary adhesive is configured to remain with an inward facing surface of a lens layer that is released from the lens stack, and wherein the intermediary adhesive on the inward facing surface of the released lens layer is sufficiently tacky to adhere to an outward surface of a subsequently released layer of the lens stack.

6. The tear-off lens capture system of claim 1, wherein a lower-most layer of the lens stack is configured to mount to the base lens of the eye protector without using pins on the base lens.

7. The tear-off lens capture system of claim 1, wherein the lens stack comprises at least two releasable lens layers laminated together with an intermediary adhesive layer between each of the releasable lens layers, and wherein a lower-most layer of the lens stack comprises an attaching adhesive layer applied about a perimeter of the lower-most layer.

8. The tear-off lens capture system of claim 7 wherein the attaching adhesive applied about the perimeter of the lower-most layer of the lens stack has a higher peel-strength than the intermediary adhesive between each of the releasable lens layers of the lens stack.

9. The tear-off lens capture system of claim 1 wherein the lens stack comprises an upper lens stack mountable to a lower lens stack, each of the upper and lower lens stack comprising a plurality of lens layers laminated together and an attaching surface on a lower surface, each of the upper lens stack and the lower lens stack having a first tab portion that forms a part of the first tab of the lens stack and a second tab portion that forms a part of the second tab of the lens stack.

10. An eye protector that captures released layers of a laminated tear-off lens stack that is mounted thereto, the laminated tear-off lens stack having at least one tab with an aperture, the eye protector comprising:
   a transparent base lens;
   a frame supporting at least a portion of the transparent base lens;
   a support configured to hold the eye protector on a wearer;
   a capturer positioned on the support, the capturer comprising a tacky pad and configured to hold a released tear-off lens layer released from the laminated tear-off lens stack along the support; and
   a retainer mounted to the frame and extending outwardly from the frame and away from the base lens, the retainer defining a slot configured to receive the at least one tab, the retainer having a holder protruding away from the slot and the base lens, the holder configured to form an engagement with the aperture on the at least one tab of the laminated tear-off lens stack.

11. The eye protector of claim 10, wherein a released lens layer of the lens stack is biased toward the support.

12. The eye protector of claim 11, wherein the released lens layer of the lens stack includes a tacky surface configured to hold a second released lens layer of the lens stack.

13. A tear-off lens capture system for use with an eye protector having a base lens and a frame supporting the base lens, the system comprising:
   a retainer configured to be mounted to an outward facing side of the frame so that the retainer extends away from the base lens, the retainer including a slot and a holder, the slot defined by an inner surface of the retainer, the slot being positioned outward from the base lens when installed on the eye protector, the holder protruding from the retainer and extending away from the base lens when installed on the eye protector; and a lens stack configured to be mounted to an outward side of the eye protector, the lens stack formed of at least one releasable lens layer, the lens stack including a central viewing area, a first tab extending from a first edge of the central viewing area, and a second tab extending from a second edge opposite the first edge of the central viewing area, the second tab having an end portion, an intermediate portion between the end portion and the central viewing area, a front side, a back side, a second tab width, and an aperture;

wherein the slot has a slot width that is at least as wide as the second tab width such that the intermediate portion of the second tab extends through the slot and at least partly around the holder, the inner surface of the retainer positioned adjacent at least a portion of each of the front side and back side of the second tab, and wherein the aperture on the second tab is configured to engage with the holder, wherein the lens stack comprises at least two releasable lens layers laminated together with an intermediary adhesive layer between each of the releasable lens layers, the inter-mediary adhesive is configured to remain with an inward facing surface of a lens layer that is released from the lens stack, and wherein the intermediary adhesive on the inward facing surface of the released lens layer is sufficiently tacky to adhere to an outward surface of a subsequently released layer of the lens stack while the second tab continues to be engaged with the holder.

14. The tear-off lens capture system of claim 13, wherein the second tab has a length configured to allow the second tab to be wound around at least a portion of the retainer so that the lens stack is placed in tension upon mounting to the eye protector.

15. The tear-off lens capture system of claim 13, wherein the intermediary adhesive layer extends between the opposing first and second edges of the central viewing area so that no intermediary adhesive layer is applied between the releasable lens layers along either the first or second tab.

16. The tear-off lens capture system of claim 13 further comprising an attaching adhesive applied about a perimeter of a lower-most layer of the lens stack that has a higher peel-strength than the intermediary adhesive between each of the releasable lens layers of the lens stack.

* * * * *